United States Patent
Nelson et al.

(10) Patent No.: US 6,204,254 B1
(45) Date of Patent: *Mar. 20, 2001

(54) BIOCOMPATIBLE SURFACES AND A METHOD FOR THEIR PREPARATION

(75) Inventors: Deanna J. Nelson, Libertyville; Ton That Hai, Mundelein; David E. Pereira, Crystal Lake; Timothy N. Estep, Grayslake, all of IL (US)

(73) Assignee: Baxter International, Inc., Deerfield, IL (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/928,841

(22) Filed: Sep. 12, 1997

(51) Int. Cl.[7] .................... A61K 31/715; A61F 2/06; C07H 1/00; C08B 37/00

(52) U.S. Cl. .................... 514/54; 514/53; 623/1; 536/1.11; 536/4.1; 536/17.2; 536/18.7; 536/20; 536/21; 536/22.1; 536/53; 536/123.1; 536/124

(58) Field of Search .................... 514/54, 53; 623/1; 536/1.11, 22.1, 4.1, 17.2, 18.7, 20, 21, 53, 123.1, 124

(56) References Cited

U.S. PATENT DOCUMENTS

| | | | |
|---|---|---|---|
| 4,613,665 | 9/1986 | Larm | 536/20 |
| 4,624,919 | 11/1986 | Kokusho et al. | 435/74 |
| 4,943,630 | 7/1990 | Jacquinet et al. | 536/123 |
| 5,354,853 | 10/1994 | Staveski et al. | 536/17.1 |
| 5,472,951 | 12/1995 | Saitoh et al. | 514/54 |
| 5,510,418 | 4/1996 | Rhee et al. | 525/54.2 |
| 5,527,893 | 6/1996 | Burns et al. | 514/53 |
| 5,605,938 | 2/1997 | Roufa et al. | 514/59 |

FOREIGN PATENT DOCUMENTS

WO 96/34889  11/1996  (WO) .................... 14/805

OTHER PUBLICATIONS

Hascall, et al., Immunology of Chondroitin/Dermatan Sulfate, in Glycoimmunology, Alavi, A. and Axford, A. S. eds., Plenum Press, New York, pp. 205–216 (1995) published sufficiently before filing date such that the month is not as issue.

Connective Tissue Proteoglycans, in The Biochemistry of Glycoproteins and Proteoglycans, W. J. Lennarz ed., Plenum Press, New York, pp. 286–314 (1980).

*Primary Examiner*—Gary Geist
*Assistant Examiner*—Everett White
(74) *Attorney, Agent, or Firm*—Senniger, Powers, Leavitt & Roedel

(57) ABSTRACT

A novel group of compounds is disclosed for decorating the surface of synthetic polymeric or tissue derived prostheses to prevent adverse rejection events. The decorating molecules are obtained as derivatives of naturally occurring polysaccharides, derivatized to provide functionally reactive groups at the termini thereof, and the reacting with nucleophilic or other groups on the surface of the prosthesis in a simple one step reaction. Some of these reagents are useful in noncovalent adsorption to polyolefinic or perfluorocarbon based materials. Finally, phospholipids partially substituted with the nonantigenic polysaccharides provide a superior bipolar component for liposome formation.

16 Claims, 10 Drawing Sheets

1. Linker No. 1

2. Linker No. 2

3. Branched Linker

BIOCOMPATIBLE SURFACES AND A METHOD FOR THEIR PREPARATION

FIELD OF THE INVENTION

This invention relates to reagents and reagent conjugates which have enhanced biocompatibility resulting from molecular masking of antigenic determinants presented on a prosthetic surface.

BACKGROUND OF THE INVENTION

The biocompatibility of materials and devices exposed to vital processes of the body is critical to their utility in therapeutic applications. More than 3 million people in the United States have long-term biomedical implants, including breast prostheses, joint replacements, vascular grafts, pacemakers and catheters, in which therapeutic efficiency is determined in part by the duration of the implant. If the exposed surfaces of these prostheses are not biocompatible, adverse reactions associated with rejection of the implant such as inflammation, necrosis, hemolysis, complement activation, cell adhesion, protein adsorption, thrombus formation, anaphylaxis, fever, calcification, rigidity, phagocytosis, antibody generation, neointimal proliferation, platelet aggregation, fibrosis, coagulation, and infection are frequent and sometimes life-threatening immune responses that may be elicited by a foreign entity. The classical foreign body reaction may not trigger the foregoing response, but will impair or occlude the function of the prosthesis.

Disruption of the endothelium is a potent stimulus for neointimal proliferation, a common mechanism underlying the restenosis of atherosclerotic vessels after balloon angioplasty. (Liu et al., *Circulation,* 79:1374–1387, 1989.) In addition, chronic inflammatory responses, accompanied by macrophage and/or foreign body giant cell accumulation, may give rise to accelerated calcification, bioprosthesis degeneration, stress cracking, or hydrolysis of exogenous synthetic polymers used in device manufacture. The implant may be poorly integrated into the tissue, and undesirable tissue contracture may result.

Biocompatible materials are constructed of synthetic polymers that are relatively inert, unreactive, and non-toxic. For example, polymers such as polyolefins are used in tubings, shunts, sutures and prosthetic valve structures. Polymethacrylates are used in the construction of membranes, controlled release hydrogels, and as vascular prosthesis coatings. A general description of many synthetic polymers useful in prosthesis construction is given in *Implantation Biology: The Host Response and Biomedical Devices,* R. S. Greco, Editor, CRC Press, Boca Raton, Fla., 1994, p.13 et seq.

In situations where bioincompatibility cannot be overcome, as where heterologous proteins or foreign body antigenic determinants are present, surfaces may be rendered more biocompatible by partial enzymatic hydrolysis of the antigenic determinants or by masking of such determinants by covalent attachment of exogenous or endogenous polymers such as polyethylene glycol (PEG) or albumin, respectively. The resultant extended circulating lifetime of heterologous cells or cellular components derivatized in this way may improve the adequacy of drug delivery, reduce the metabolic demand on the body, or prevent undesirable blockade of the reticuloendothelial system.

The term bioprosthesis refers to devices derived from biological tissue that is treated to impart in vivo durability. In this process, the treatment invalidates the regenerative properties of the tissue. This characteristic distinguishes bioprostheses from treatments which are meant to retain the cell-regenerative capability of the tissue, such as cryopreservation. Examples of bioprostheses include heart valves, vascular grafts, biohybrid vascular grafts, ligament substitutes, and pericardial patches. When animal tissue is used, it is termed a xenograft, while with human tissue, it is either an autograft (derived from the patient) or a homograft.

Many prosthetic implants are fabricated from donor tissues. These tissues must be stabilized to prevent their disintegration, since the collagen component begins to deteriorate almost at once. Methods for stabilization of collagenous tissue are available. (Khor, E., "Methods for the treatment of collagenous tissues for bioprostheses", *Biomaterials,* 18: 95–106, 1997.) Stabilizing tissue involves a process yielding a non-viable biohomologous material by promoting bonds between functional groups of the amino acids contained in the tissue. Chemical methods typically utilize bifunctional reagents that interact with collagen at two different sites to give rise to cross-links between two collagen molecules.

One of the most widely used reagents for tissue treatment is glutaraldehyde. (Jayakrishnan A, Jameela SR, "Glutaraldehyde as a fixative in bioprostheses and drug delivery matrices", *Biomaterials,* 17: 471–484, 1996.) Since 1960, when this chemical agent was first used, many variations and conditions have been applied to optimize its efficiency. In fact, glutaraldehyde is the only agent used commercially to treat bioprosthetic tissues.

Despite its broad utility, glutaraldehyde has a number of shortcomings. The most serious of these is tissue calcification after implantation, a process that is the predominant cause in the failure of porcine aortic valves and bovine pericardium bioprostheses.

Attempts to control calcification include strategies for interrupting or retarding one or more steps in the calcification process. For example, the use of surfactants in tissue treatment is believed to control calcification by removing phospholipids. Other agents which have been employed to increase biocompatibility include sole or continued use of diphosphonates, amino-oleic acid, dimethyl sulfoxide, polyglycidyl ethers, and metal ions. However, none of these treatments has proven sufficiently beneficial to gain regulatory approval and general clinical use, and their applications are confined to laboratory models.

If these strategies are not used, these materials, bioprostheses, or moieties, like any foreign body, trigger acute inflammatory responses that may be followed by chronic inflammation and rejection. (Tang, L, Eaton, JW, "Inflammatory Responses to Biomaterials", *Am. J. Clin. Pathol.,* volume 103 (no. 4), 466–471, 1995.) In general, in these processes a layer of host proteins accumulate on the surface and rapidly denature and degrade. As a result, large numbers of phagocytic cells are attracted to and bound to the site. These phagocytes, perhaps with the collaboration of other cells, initiate inflammatory and fibrotic responses that have both short- and long-term adverse effects on the host.

New approaches are needed for rendering surfaces biocompatible. This need extends to both artificial prosthetic surfaces and also to bioprosthetic tissues, for methodology by which bioprosthetic tissues may be treated to maintain structural and functional integrity for long periods of time following implantation in vivo.

SUMMARY OF THE INVENTION

For many medical conditions there is no available substitute for the implantation of prosthetic devices in the body.

Many of these are made of plastic such as immunoisolation chambers, joint parts, bone replacements, or other polymer fabrics. Other prostheses are derived from human or animal tissue such as heart valves, skin, etc. While some prostheses are intended only for short term use (as an artificial heart), others will reside in the body indefinitely.

It is an object of the present invention to provide a decorating molecule capable of disguising or masking determinants on prosthetic surfaces which induce immune or sensitization responses leading to eventual rejection or failure of the prosthesis. It is a further object to provide a coating of negative charge which will help to repel red blood cells and platelets, whose contact with prostheses leads to immune activation. It is a still further object to devise chemistries that permit covalent or noncovalent attachment between the protective decorative molecule and the prosthetic surface.

In accordance with the invention, polysaccharides containing a linker and reactive groups for combining chemically with moieties on the surface of prostheses of either tissue or synthetic origin are derived by hydrolysis from chondroitin or hyaluronic acid. These compounds are ubiquitous in the mammalian body, and are not perceived by the immune system as antigenic because of their prevalence in the tissues and the high level of access of the molecules to the blood.

These polysaccharides may be broken down into oligosaccharides of repeating sugar units, and the reducing end may be modified chemically to react with groups capable of attaching to the surface of prothesis. It is desirable also to include a linker, also of benign immunogenicity (e.g. of low antigenicity or not immunogenic in the species to which it is administered), to prevent steric hindrance between the reactive group on the oligosaccharide linker molecule and a nucleophilic group on the substrate therapeutic agent surface.

Compounds are provided with the following formula I:

wherein A and B are sugars which may be of N-acetylgalactosamine, N-acetylglucosamine, glucuronic acid, iduronic acid or glucose forming a repeating disaccharide unit in which A and B are joined covalently by a glycosidic bond between C-1 of sugar A and C-3 or C-4 of sugar B. The A—B disaccharide units are joined covalently to form an oligosaccharide by a glycosidic bond between C-1 of penultimate sugar B of a first disaccharide unit and C-3 or C-4 of sugar A in the next successive disaccharide unit. B' is a sugar at the non-reducing terminus of the oligosaccharide of ring structure identical to sugar B, and A' is a 1-amino, 1-amido, or 1-imino acyclic hexose joined covalently by a glycosidic bond between C-1 of sugar B at the terminus opposite the non-reducing terminus of said oligosaccharide and C-3 or C-4 of sugar A'. This structure is further joined covalently by a 1-amino, 1-amido, or 1-imino linkage to linker L comprising an aliphatic, acyclic carbon chain containing one or more moieties, which can be an ether, thio ether, or amide. The linker bridges sugar A' and one or more electrophilic groups Z, which may be an aldehyde, an activated ester of a carboxylic acid, a maleimide, an epoxide, a tosyl or tresyl ester, or a halide.

The foregoing compounds are constructed from oligosaccharides which may be derived from chondroitin-4-sulfate, chondroitin-6-sulfate or hyaluronic acid. "Derived" herein means hydrolyzing these native polysaccharides by acid hydrolysis, down to oligosaccharides of a molecule size range of 1,000 to 15,000 Daltons.

Oligosaccharide-polymer conjugates for masking biologically reactive sites on the surface of prosthesis have the structure of the masking molecule set forth above and a formula II:

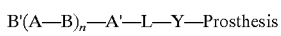

wherein the letter symbols have the structures stated in the above disclosure, and Y is selected from a methylene radical, beta-hydroxyethylene radical, carboxyl radical, succinimide alpha radical, and nullity. The method of making these conjugates is a simple one step reaction in which the polysaccharide reagents set forth above are reacted with the nucleophilic moieties such as an amino or sulfhydryl group presented in abundance on the surface of the prosthesis, either a synthetic polymer surface or surface derived from tissue.

The polysaccharides having a terminus consisting of either an n-alkyl group of 5 to 30 carbon atoms, or a perfluorinated tail group, also of 5 to 30 carbon atoms are useful in decorating a polyolefinic or perfluorocarbon based prosthesis respectively. These alkyl or perfluorinated tails are added to the linker by conventional chemistries.

Finally, the present invention provides a novel "stealth" type liposome, capable of delivering a therapeutic agent on a continuous basis, or by repeated administration, without causing immune mediated reactions. The liposome contains one or more phospholipids in which one fatty acid in the 1 or 2 carbon position on the glycerol backbone is substituted with the polysaccharide-linker substituents set forth above. The composition of the lipid fraction may either be defined by hydrolyzing all the ester bonds, removing the released fatty acids, and then re-esterifying in the desired position by a fatty acid of defined structure, or a group of fatty acids of desired ratio. Alternatively, the naturally occurring fatty acids at a given desired position can be retained, and the polysaccharide substituted at the open position. These liposomes will contain the usual mixture of phopholipids, cholesterol, and an aqueous component or phase, in addition to the present substituted phospholipid, and be made according to a variety of conventional liposome forming methods.

DETAILED DESCRIPTION OF THE PREFERRED EMBODIMENTS

Surface modification according to the method of the present invention provides a biocompatible surface having exposed polyanionic polysaccharide moieties that are structurally and functionally similar to natural polymers found in the mammalian body. The disperse negative charge of the polyanionic surface will repel like-charged cells in the body, such as red blood cells, for example, thereby minimizing adverse interactions with such cells. The polyanionic polysaccharide nature of these derivatized surfaces have the characteristics of a hydrogel, and imbibe and maintain water. Moreover, the polyanionic polysaccharide surfaces are space-filling. The similarity of the polyanionic polysaccharide-conjugated surface of the instant invention promotes favorable interactions (in-growth, for example) with similar natural surfaces in the body. These biocompatible surfaces are very similar to macromolecular glycosaminoglycan substances that the biological environment recognizes and deals with metabolically. Problems of toxicity and stimulation of adverse inflammatory or immune reactions are suppressed.

Surface modification with the polyanionic polysaccharide may be used with devices and machines, tissues, bioprostheses, xenografts, cells, cellular constructs such as liposomes or vesicles, or the like, and therefore is intended to be used to decorate surfaces of both synthetic polymer and tissue derivation.

Figure 1A:
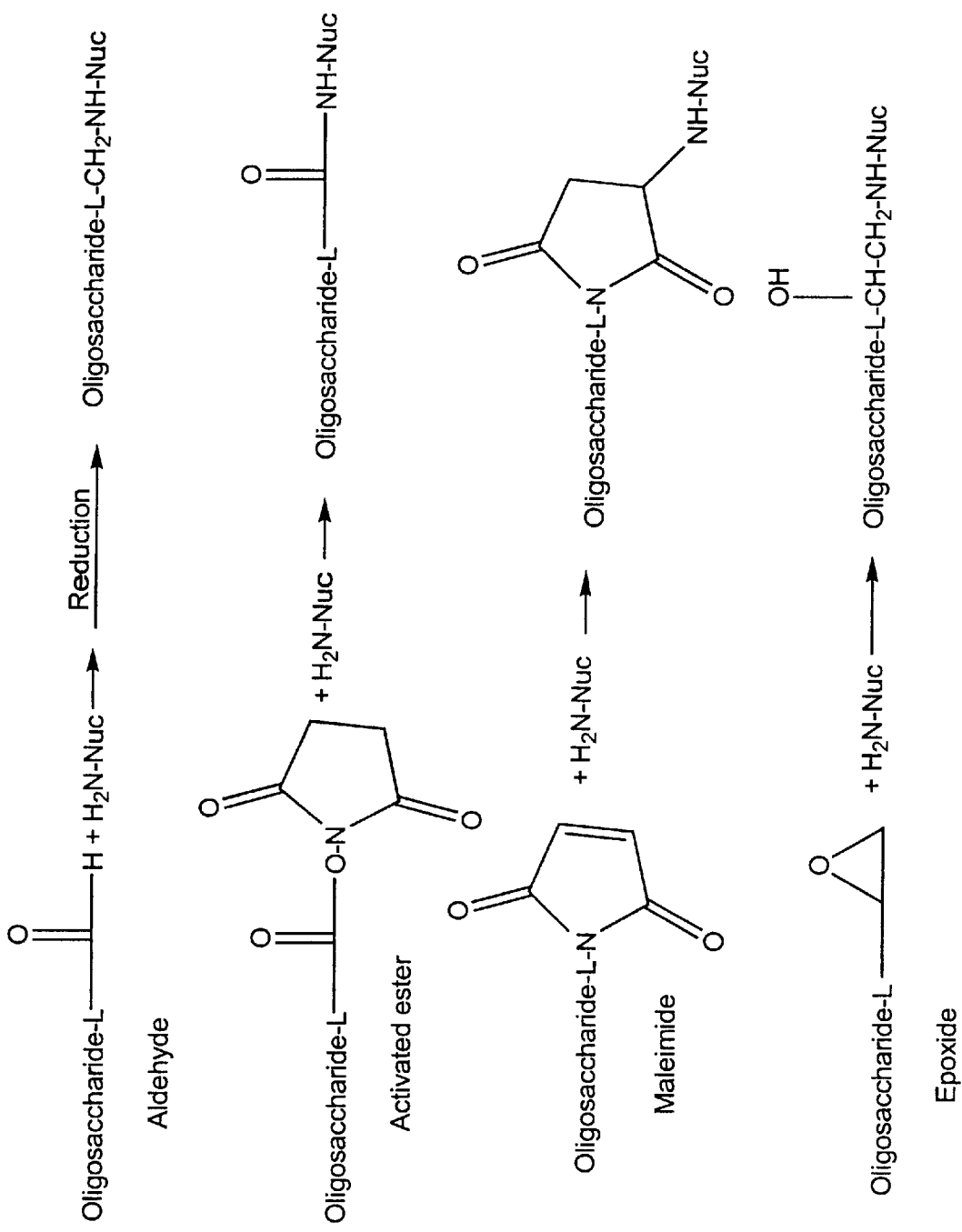
FIGS. 1A and 1B are lists of reactions showing the condensation of polysaccharides having various reactive termini with nucleophilic moieties on the surface of prostheses.
Figure 1B:
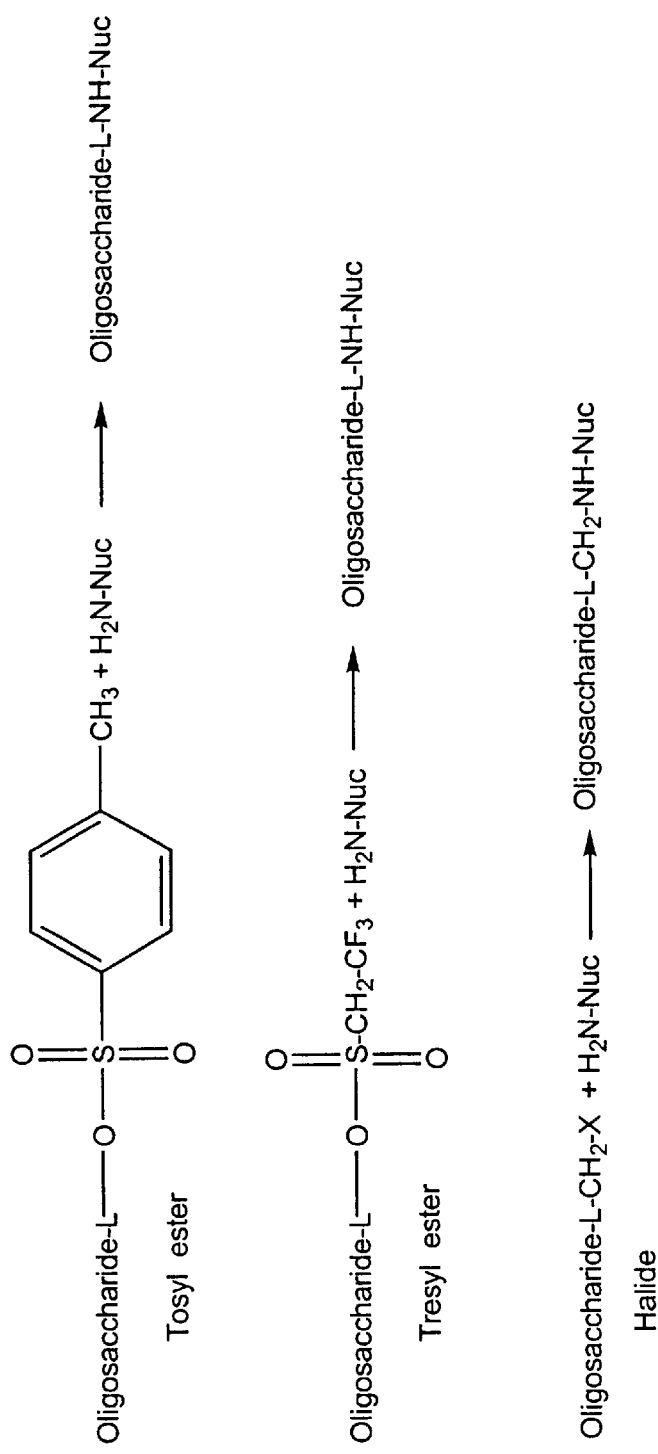
Figure 2:
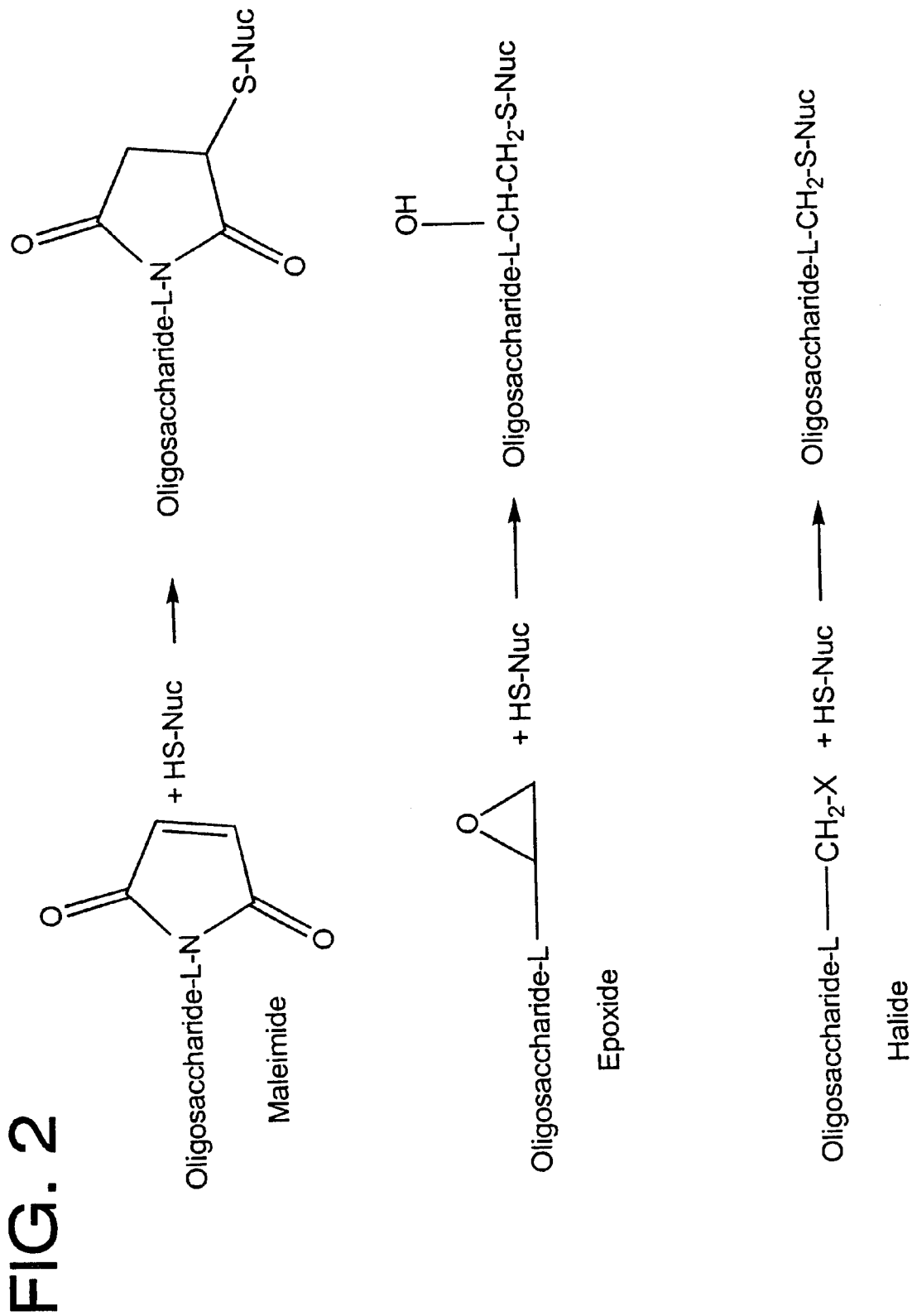
FIG. 2 is a list of reactions showing the condensation of polysaccharides having selected reactive leaving groups with sulfhydryl groups on the surface of prostheses.
Figure 3:
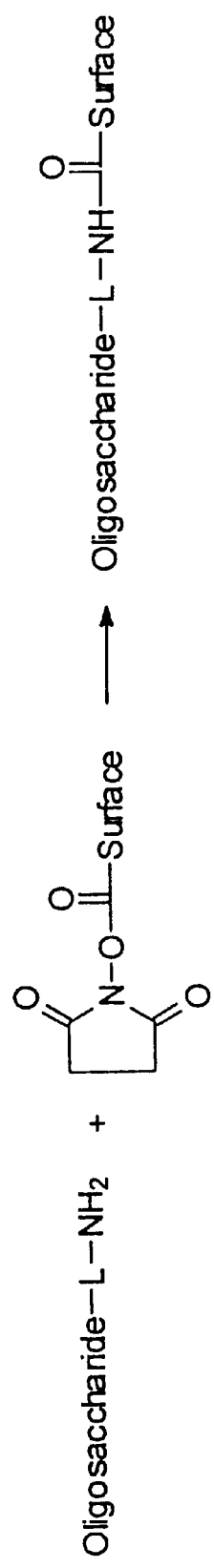
FIG. 3 shows the reaction of an oligosaccharide having a free amino group with a surface group having a reactive leaving group.

In a preferred embodiment, a polyanionic polysaccharide reagent molecule is covalently joined to a prosthetic surface. Typically, the decorating polysaccharide is joined by reaction of a terminal electrophilic moiety on the polysaccharide, such as an activated ester, aldehyde, maleimide, epoxide, a tosyl or tresyl ether, or a halide with nucleophilic moieties such as an amino or sulfhydryl group on the surface of the prosthesis. FIGS. 1A, 1B and 2 illustrate a number of examples of the structures of reactants and conjugates formed by reaction for both amino and sulfhydryl containing surfaces. FIG. 3 illustrates the reverse reaction in which the nucleophilic amino group is positioned at the terminus of the polysaccharide linker.

Figure 4:
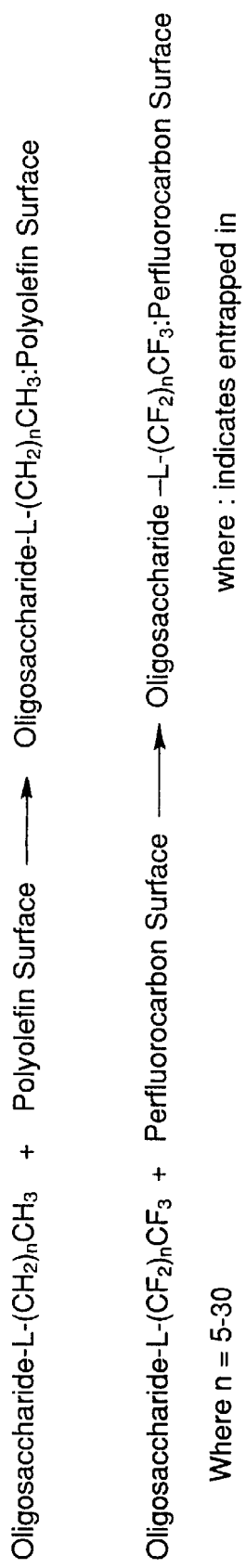
FIG. 4 shows the adsorption of oligosaccharides having a terminal alkyl or perfluorinated group onto polyolefinic or perfluorocarbon surfaces, respectively.

In addition to covalent attachment of the polysaccharide to the prosthetic surface, non-covalent interactions to form stable complexes of the polysaccharide moiety to the polymer surface have efficacy. Polyolefinic substrates will readily adsorb oligosaccharides or polysaccharides having a saturated n-alkyl tail in place of a reactive electrophilic group. Similarly, a perfluorocarbon surface will readily absorb or entrap oligosaccharides or polysaccharides having a perfluorinated radical tail. The tails contain 5 to 30 carbon atoms, and have the structures represented in FIG. 4. Typical polyolefinic plastics used extensively in prosthetic applications, which are useful when masked by polysaccharides, are the polyethylenes and polypropylenes. A typical perfluorocarbon based plastic is perfluorinated polypropylene.

The polysaccharide reagents may also be utilized in making liposomes for a wide range of applications including delivery of therapeutic agents. Liposomes have a structure in which phospholipid bilayers have interspersed aqueous compartments. Sometimes multilayer concentric structures can be formed. In many of the delivery systems in which therapeutic agents can be made available to cells, several problems arise. For example, the drug to be delivered is water based, and cannot penetrate the lipids comprising the cell membrane, or the drug is degraded in free solution too quickly to be of benefit. A still further problem is that repeated administration of many liposome structures results in immunization or sensitization to the liposome material. A great advantage of the liposomes of the present invention is that the hydrophilic fraction of the phospholipid conferring the predominant charged domains is a substituted phospholipid having the structures:

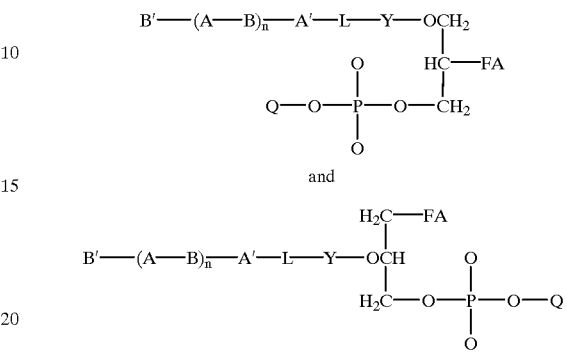

and in which FA is a fatty acid, Q is selected from the group consisting of choline, ethanolamine, serine, or inositol; and A and B are sugars forming a repeating disaccharide unit in which A and B are joined covalently by a glycosidic bond between C-1 of sugar A and C-3 or C-4 of sugar B, and the A-B disaccharide units are joined covalently to form an oligosaccharide by a glycosidic bond between C-1 of penultimate sugar B of a first disaccharide unit and C-3 or C-4 of sugar A in the next successive disaccharide unit, B' is a sugar at the non-reducing terminus of said oligosaccharide of ring structure identical to sugar B, A' is a 1-amino, 1-amido, or 1-imino acyclic hexose joined covalently by a glycosidic bond between C-1 of sugar B at the terminus opposite the non-reducing terminus of said oligosaccharide and C-3 or C-4 of sugar A', and further joined covalently by a 1-amino, 1-amido, or 1-imino linkage to linker L comprising an aliphatic, acyclic carbon chain containing one or more moieties selected from the group consisting of ether, thio ether, and amide, wherein said linker bridges sugar A' and a terminal group and Y is an acyl radical.

The substituted phospholipid can be a homogeneous or very diverse population. Well known techniques are available conventionally in the art to effect entire or only partial hydrolysis of the fatty acid ester bonds. Further, such techniques are available for selective partial hydrolysis at either the 1 or 2 position of the glycerol backbone. To be miscible with both the hydrophobic and hydrophilic fractions of the liposome, there should be at least one fatty acid in the construct. Following selective partial hydrolysis, the polysaccharide portion can be added as by the reactions available conventionally for condensation of the hydroxyl group of the glycerol and the electrophilic group of the polysaccharide reagent. For a reference on the role of vesicle lipid composition on the incorporation properties of the liposome into cells, see Poste, et al., *PNAS*, 73: 1603 (1976).

Figure 5:
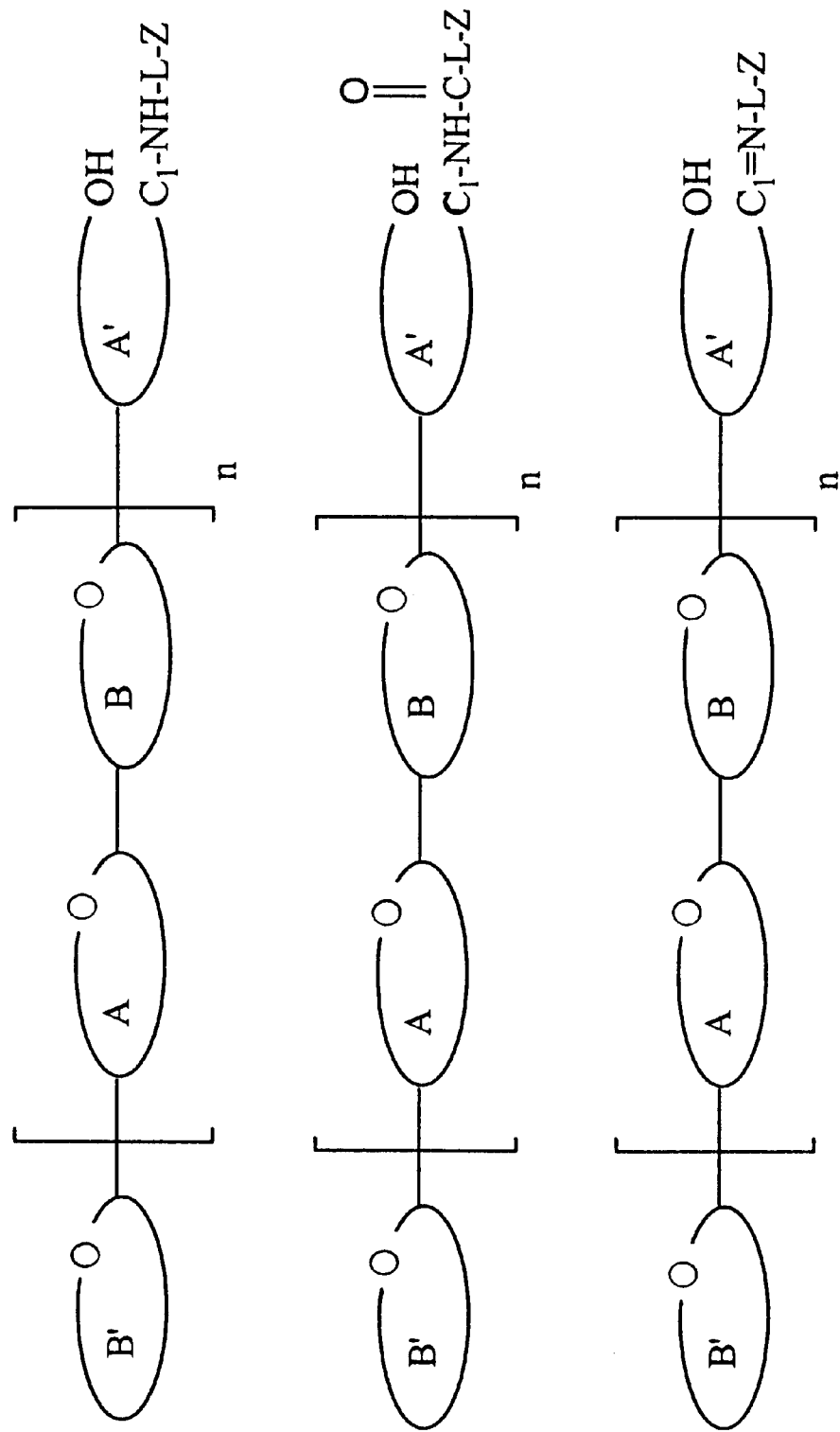
FIG. 5 is a ring structure schematic of the polysaccharide reagents capable of reacting with nucleophilic surface groups on prostheses.

In FIG. 5, each ring structure A, A', B and B' is a sugar. Each sugar contains at least one substituent selected from the group consisting of $-CO_2^-$, $-OSO_3^-$, $-NHCOCH_3$, and $-NHSO_3^-$. The remaining substituents on the sugar ring are selected from the group consisting of $-H$, glycosidic $-O-$ and $-OH$. The repeating unit of the oligosaccharide comprises sugar A and sugar B, wherein sugar A is covalently joined to sugar B by a glycosidic bond from carbon-1 of sugar A to carbon-3 or carbon-4 of sugar B, wherein sugar B is covalently joined sugar A by a glycosidic bond from carbon-1 of sugar B to carbon-3 or carbon-4 of sugar A, and n is an integer from 2 to about 20. Sugar B', which is positioned at the non-reducing terminus of the oligosaccharide has a structure identical to that of sugar B, with the exception that it is not covalently joined by a glycosidic bond at carbon-3 or carbon-4 to any other sugar. Sugar A', the erstwhile reducing sugar of the oligosaccharide, has a structure identical to that of sugar A, with the exception that the latent aldehyde that was present at carbon-1 of the sugar has been modified by reductive amination or imination to enable covalent joining to one terminus of a linker L.

The sugars A, A', B, and B' which are useful in the present invention may be commonly named as, for example, N-acetylglucosamine, glucuronic acid, N-acetygalactosamine, iduronic acid, and glucose.

Linker L is an organic bridge having a length of from about 10 Å to about 300 Å and having a plurality of termini, one of which is covalently joined as an amine or imine to carbon-1 of sugar A' and each of the remainder of which terminates as and is covalently joined to Z, an organic functionality which provides a reaction group for covalent coupling to a nucleophile.

The organic bridge of linker L may be an acyclic, aliphatic carbon chain containing ether, thioether, or amide moieties and has a linear portion extending from sugar A' and a linear or branched portion that incorporates the remaining terminus or termini.

Figure 6:
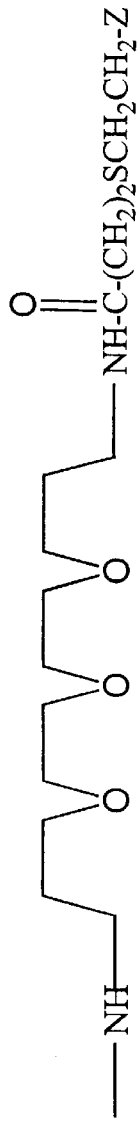
FIG. 6 gives the structure of three typical linkers for covalently attaching the polysaccharides to a surface.
Figure 6:
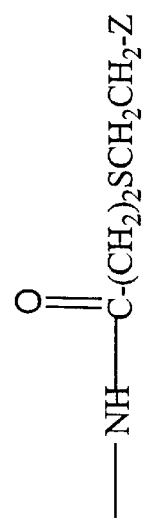
Figure 6:
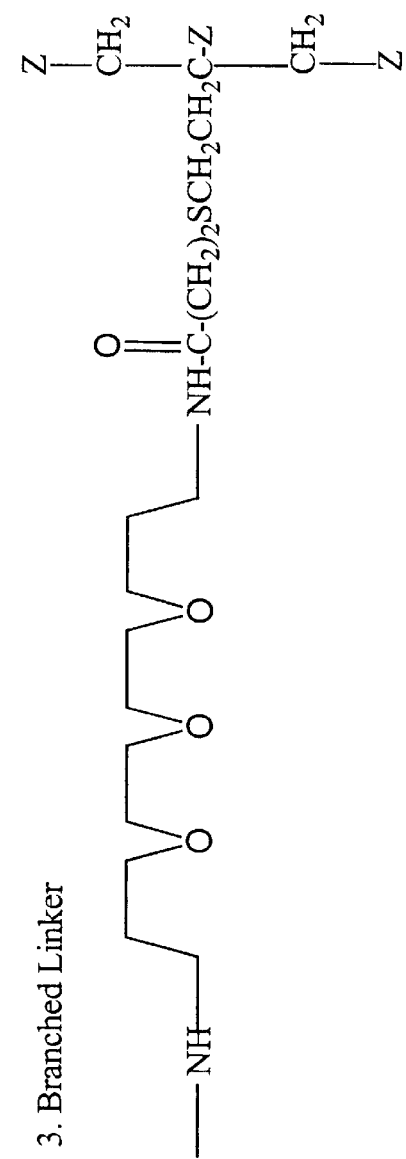

The purpose of the linker is to position the reactive group away from the oligosaccharide chain so as to avoid steric hinderance of the coupling reaction forming the conjugated macromolecule. It is important that the linker be aliphatic and acyclic with an absence of double bonds or aromatic rings. The incorporation of ethylene or diethylene glycol moieties, amide bonds, and thioether groups reduces antigenicity and provides for water solubility. The linker may contain one or more of these moieties as illustrated in the structures set forth in FIG. 6. The linker may be completely linear or may be branched at the terminus opposite its point of covalent attachment to sugar A'. The branched termini may each end in a Z group, to create a plurality of attachment points between the macromolecular surface and the oligosaccharide strand.

An organic functionality Z is covalently joined to each free terminus of linker L joined to sugar A'. Functionality Z will react with a nucleophile to form a covalent bond between a reagent of the present invention and the nucleophile. For example, if Z is an aldehyde, an activated ester of a carboxylic acid, a maleimide, an epoxide, a tosyl or tresyl ester, or a halide, such a reagent of the present invention will react with an amine nucleophile to yield a product in which the said reagent is covalently joined to an amine nucleophile as an imine or amine (after reduction), an amide, an amine-substituted maleimide, a beta-hydroxy amine, or an amine, respectively (see FIG. 1 for typical reactives). A Z halide, maleimide, or epoxide will also react with a sulfhydryl nucleophile to yield a product covalently joined to the sulfhydryl nucleophile as a sulfide, a thio-substituted maleimide, or a beta-hydroxy sulfide, respectively.

Many examples of these chemistries are given in *Chemistry of Protein Conjugation and Cross-linking,* S. Wong, CRC Press, Inc. (1991) which is incorporated by reference herein.

The molecular weight of the reagents of FIG. 5 is from about 1,000 to about 15,000 Daltons, more preferably from about 1,000 to about 10,000 Daltons, and most preferably about 5,000 Daltons. The oligosaccharide component of Formula I may be synthesized de novo or may be derived from natural sources. In a preferred embodiment, the oligosaccharide is a hydrolysate of chondroitin sulfate. The hydrolysis is carried out conventionally, and the fragments may be sorted by known sizing methods to produce a population of desired length having less than five percent contamination by oligosaccharides of a length different from the desired length.

Substrates suitable for modification by the present reagents include peptides, proteins, nucleotides, polynucleotides, pharmaceutic agents, diagnostic agents, and polymers which have at least one nucleophilic functional group capable of forming a covalent bond with the terminus of the linker.

Figure 7:
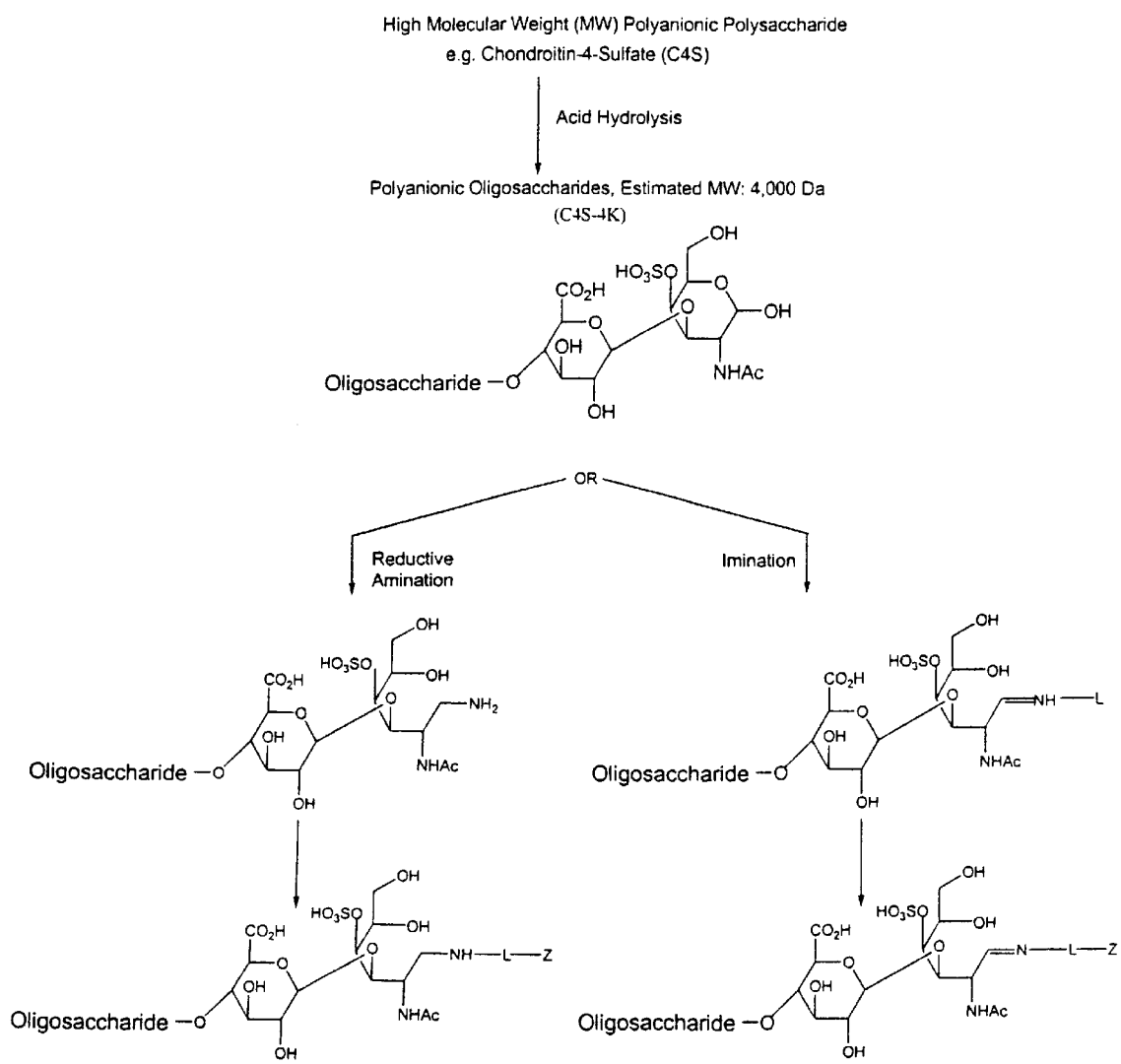
FIG. 7 is a structural schematic of the production of a suitable polysaccharide from chondroitin-4-sulfate.
Figure 8:
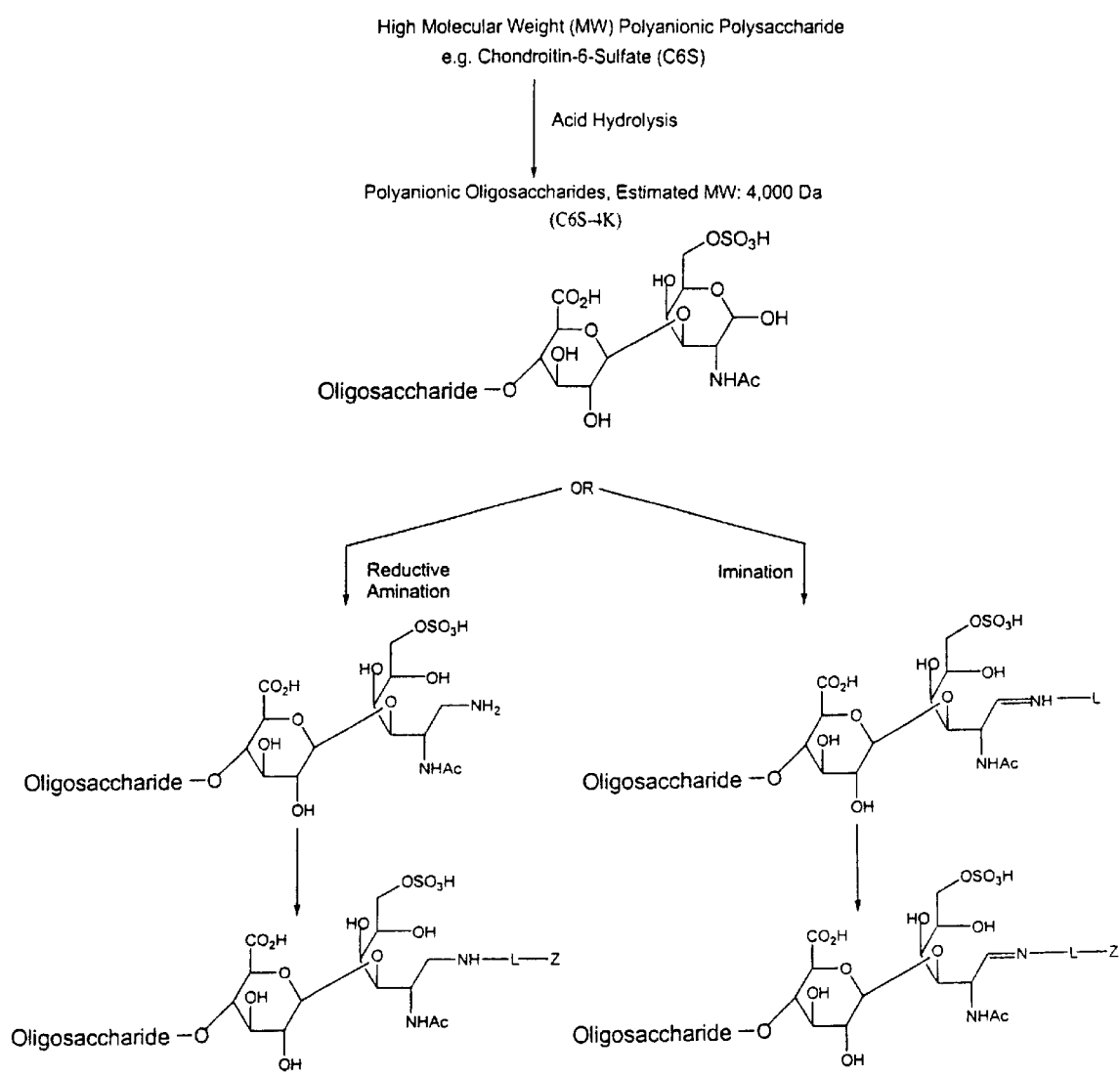
FIG. 8 is a structural schematic of the production of a suitable polysaccharide from chondroitin-6-sulfate.
Figure 9:
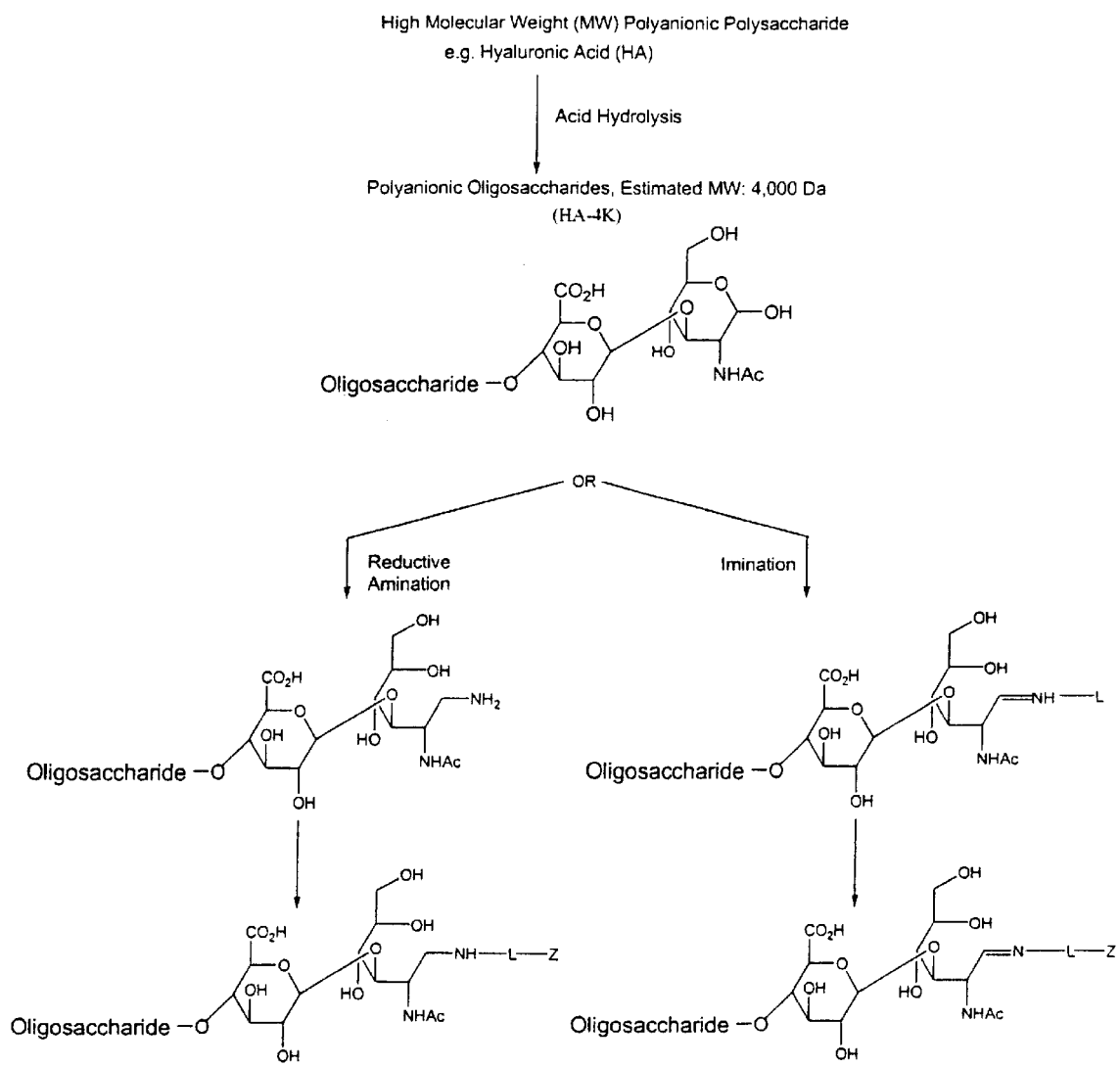
FIG. 9 is a structural schematic of the production of a suitable polysaccharide from hyaluronic acid.

FIGS. 7–9 are flow diagrams showing structures of compounds provided in the reaction pathway in the synthesis of three reagent compounds. In FIG. 7 the starting material is an acid hydrolysate (polyanionic oligosaccharides) derived from chondroitin-4-sulfate. The terminal sulfate sugar is converted by reductive amination or imination to the structures shown, and then further reacted with the linker moiety containing a Z reaction group. Z reaction groups comprise an aldehyde, activated ester of a carboxylic acid, maleimide, tosyl ester, tresyl ester, halide, or epoxide. As depicted in the equations shown in FIGS. 1A, 1B and 2, the Z group reacts with either an amino nucleophile or sulfhydryl nucleophile to form a bond covalently coupling the oligosaccharide linker moiety to the protein or other macromolecule.

The polyanionic oligosaccharide portion of the reagents is selected to mimic the structure and properties of glycosaminoglycans found naturally in the extracellular matrix. Thus, the polyanionic oligosaccharides are linear sugars, have a non-reducing terminus and a terminus opposite the non-reducing terminus, and are constructed from a repeating disaccharide unit. The two sugars of the disaccharide unit are joined covalently by a glycosidic bond between C-1 of one sugar and C-3 or C-4 of a second sugar and each sugar of each repeating disaccharide unit is joined covalently by a glycosidic bond to another sugar.

The oligosaccharide portion of the reagents may be obtained by acid or enzyme catalyzed hydrolysis of natural polysaccharides or may be synthesized de novo. For example, the polyanionic polysaccharides chondroitin 6-sulfate, chondroitin-4-sulfate or hyaluronic acid may be hydrolyzed with acid catalysis to a mixture of polyanionic oligosaccharides and the fragments may be sorted by known sizing methods to produce a population of desired length. In the case of chondroitin-6-sulfate the repeating disaccharide is N-acetylgalactosamine-6-sulfate joined covalently by a glycosidic bond to glucuronic acid.

In the case of chondroitin-4-sulfate the repeating disaccharide is N-acetylgalactosamine-4-sulfate joined covalently by a glycosidic bond to glucuronic acid. In the case of hyaluronic acid the repeating disaccharide is N-acetylglucosamine joined covalently by a glycosidic bond to glucuronic acid.

Likewise, starch may be hydrolyzed with acid or enzyme catalysis to a mixture of oligosaccharides and the fragments may be sorted by known sizing methods to produce a population of desired length. The selected population of fragments may be sulfated by conventional means to produce a polyanionic oligosaccharide having repeating disaccharide units comprised of glucose and sulfated glucose joined covalently by glycosidic bonds.

FIGS. 8 and 9 show the reaction and compounds formed where the starting materials are acid hydrolyzed chondroitin-6-sulfate and hyaluronic acid, respectively. In each case, a linker has a Z reaction group at its non-sugar terminus.

The reagent structures discussed above will be useful in reactions with surfaces, especially tissue derived prostheses, which have an abundance of surface nucleophilic sites. These reagents and their synthesis and chemical properties have been described in detail in our co-pending U.S. application Ser. No. 08/897,336, filed Jul. 21, 1997, now U.S. Pat. No. 6,018,035, hereby incorporated by reference, particularly in the Examples set forth therein. After reaction, the Z group is lost and the prosthetic surface is joined covalently to the polysaccharide via the linker L and the coupling structure Y. The terminal group Y is selected from the group consisting of a methylene radical, beta-hydroxyethylene radical, carboxyl radical, succinimide alpha radical, and nullity (no portion of the reacting group becomes a part of the condensed molecule). The final structure may be represented as B'—(A—B)$_n$—A'—L—Y—Prosthesis, with the letter symbols representing the structures set forth above.

The method of masking biologically reactive sites on the surface of polymeric synthetic or tissue derived prostheses comprises the simple step of reacting the masking molecule polyanionic polysaccharide reagent disclosed above with nucleophilic moieties on the surface, and optionally washing away the unreacted reagents. The reaction between the electrophilic Z' group selected from an aldehyde, activated ester of a carboxylic acid, maleimide, epoxide, a tosyl or tresyl ester, or halide, and the nucleophilic group proceeds rapidly and can be driven essentially to completion. The details are set forth in the Examples of U.S. Pat. No. 6,018,035.

EXAMPLES

Example 1

In vitro Exposure of Oligosaccharide-Modified DCLHb to Red Cell Preparations.

Approximately 20 mL of human blood was freshly collected from each of several donors into an evacuated container containing ethylenediaminetetraacetate (EDTA). The blood samples from several donors were pooled in a 50 mL centrifuge tube. One milliliter portions were dispensed into several test tubes. Then a volume of electrolyte diluent (negative control) and a volume of a second test or control solution was added such that the final concentration of the test or control article was that shown in the following table. Another modified hemoglobin which is known to cause red cell aggregation and platelet clumping in this test was employed as a positive control. The test tubes were incubated for one hour. A specimen was removed from each test tube, and a slide was prepared from that specimen and stained. Each slide was observed for red cell aggregation and scored on a scale from zero to three, where zero indicated that no aggregation was observed and three indicated that extensive, irreversible aggregation was observed, i.e., disaggregation was not observed following the addition of normal saline solution to the sample.

TABLE 1

Results of in vitro Red Cell Aggregation Testing

| Negative Control Article and Relative Concentration by Volume | Test Article and Relative Concentration by Volume | Extent of Red Cell Aggregation |
|---|---|---|
| 50% Electrolyte Diluent | | No aggregation observed (0) |
| | 10% Positive Control | Few aggregates observed (1) |
| | 30% Positive Control | Many red cell aggregates (1+) |
| | 50% Positive Control | Extensive red cell aggregation and some small platelet clumps observed (2+) |
| | 10% C4S-4K-DCLHb | None seen (0) |
| | 30% C4S-4K-DCLHb | None seen (0) |
| | 50% C4S-4K-DCLHb | None seen (0) |
| | 10% HA-4K-DCLHb | None seen (0) |
| | 30% HA-4K-DCLHb | None seen (0) |
| | 50% HA-4K-DCLHb | None seen (0) |

In addition, this test was repeated using each of four C4S-4K-DGBE-TPA-DCLHb test articles, as disclosed in the synthesis protocols of the Examples in U.S. Pat. No. 6,018,035, having differing extents of hemoglobin modification. In each test, no red cell aggregation was observed in test solutions containing the oligosaccharide reagent-modified hemoglobin. The negative and positive control solutions gave characteristic responses.

The absence of red cell aggregation and platelet clumping by the C4S- and HA-modified hemoglobins clearly demonstrates that their biocompatibility was enhanced relative to that of the positive control modified hemoglobin.

Example 2

Test Materials

Porcine aortic valves are used as model bioprosthetic tissues.

Control tissues are prepared using current technology. Test tissues are prepared by the methodologies described below.

Test Methods

1. In vivo tests.
   A. Rat subcutaneous implant model. Briefly, two subdermal pouches, separated by at least 2 cm, are dissected in the abdominal walls of ketamine-anesthetized rats (male, 4–5 weeks, 80 g). A piece of 1×2 cm$^2$ tissue is implanted in each pocket (one control and one test specimen). The implants are retrieved after three weeks and are rinsed with distilled, deionized water and freeze dried. The amounts ($\mu$g per mg dry tissue weight) of calcium and phosphorus are to be determined by inductively coupled plasma atomic emission spectroscopy (ICP-AES) on aliquots of 6 N HCl hydrolysates of dried tissue.
   B. Canine A-1 shunt. One control and one test porcine aortic valve leaflet are sutured into the lumen of a Gore-Tex vascular graft (length 8 cm i.d.) with a separation of about 3 cm. After the function of the valves is pretested, the leaflets are sterilized with ethylene oxide gas and implanted into a mongrel dog (40 kg) as an A-I shunt between the abdominal aorta and left iliac artery. The specimens are to be retrieved after six weeks and rinsed with distilled, deionized water and freeze dried. The amounts (µg per mg dry tissue weight) of calcium and phosphorus are determined by inductively coupled plasma atomic emission spectroscopy (ICP-AES) on aliquots of 6 N HCl hydrolysates of dried tissue.

C. Canine RV-PA shunt. A Gore-Tex vascular graft containing a control or test porcine aortic valve are implanted into a mongrel dog (50 kg) between the pulmonary artery and the right ventricle. The specimens are retrieved after ten weeks and rinsed with distilled, deionized water and freeze dried. The amounts (µg per mg dry tissue weight) of calcium and phosphorus are to be determined by inductively coupled plasma atomic emission spectroscopy (ICP-AES) on aliquots of 6 N HCl hydrolysates of dried tissue.

2. In vitro tests

A. Determination of extent of glutaraldehyde crosslinking and changes in lysine content is made by amino acid analysis of hydrolysates of dried tissue.

B. Determination of the shrinkage temperature of the tissues is made using differential scanning calorimetry.

C. Determination of the mechanical strength of the tissues is made.

D. Determination of the relative resistance to collagenase digestion is made.

Tissue Modification

Two novel reagents are to be used in tissue modification. These reagents are polyanionic polysaccharide derivatives that are identified by the acronyms "CS—NH$_2$" and "HA—NH$_2$". Modification of the tissue involves the direct coupling of CS—NH$_2$ or HA—NH$_2$ into tissue (collagen). Tissues are stored in 0.20–0.65% glutaraldehyde solution at 4° C. for 1 week. A 5 g/dL solution of CS—NH$_2$ or HA—NH$_2$ in 0.1 M sodium borate buffer, pH 7.4, is prepared. Likewise, 5 g/dL solutions of CS—NH$_2$ or HA—NH$_2$ in 0.1 M sodium borate buffer, pH 8.5 and 11, are prepared. Then the tissue is to be incubated in 5% CS—NH$_2$ or HA—NH$_2$ solution for two days. The tissues are rinsed ten times with phosphate-buffered saline and then will be placed in 0.01 M NaBH$_4$ solution at 4° C. for 16 hours. The tissues will be rinsed ten times with phosphate-buffered saline. A bioprosthetic tissue control (BT control) is prepared by exposing tissue to similar conditions, but in the absence of CS—NH$_2$ or HA—NH$_2$.

Test Criteria

Tissues will be prepared according to the modification protocol described above. Each of the tissues will be characterized by the in vitro tests described above. Observation of a higher shrinkage temperature, increased mechanical strength, and higher resistance to collagenase digestion will be judged as demonstrations of improved tissue stability. An observation of lower concentrations of calcium and phosphorus, together with a ratio of calcium to phosphorus which is lower than 2.16 (that of hydroxyapatite), in tissues which have been implanted in vivo and recovered will be interpreted as indicative of lower calcification.

If these preliminary results indicate improved structural and functional performance, further testing will be implemented according to protocols to be written at that time.

Example 3
Biocompatible Red Blood Cells

Four units of packed red blood cells are pooled and diluted in three volumes of lk saline solution. An aqueous solution of CS—4K—NH—CO—(CH$_2$)$_8$CH$_3$ having a pH of about 7.3–7.5 are added and the suspension is agitated gently for a period of 24 hours. Then the red cells are diafiltered against a PlasmaLyte™ A solution using a 500,000 Dalton molecular weight cut-off membrane filter until the saline solution has been exchanged for PlasmaLyte™ A solution. The cells are to be concentrated by centrifugation and excess solution expressed from the preparation.

The biocompatibility of the modified red cells with red cells having a different blood type will be assessed using standard blood typing procedures.

Example 4
Biocompatible Liposomes

CS-modified-distearoyl phosphatidylethanolamine is prepared by reaction of CS—4K—CO—N-oxysuccinimide with lyso-distearoyl phosphatidylethanolamine. Liposomes are prepared by micro-fluidization (emulsification) of a composition of CS-modified-distearoyl phosphatidylethanolamine/hydrogenated soy phosphatidylcholine/cholesterol in molar proportions of 5:55:40, respectively.

The blood circulation half-lives of the biocompatible liposomes in mice are assessed. It is anticipated that the blood circulation half-lives of the biocompatible liposomes will be significantly longer than those of liposomes formulated without the CS-modified-distearoyl phosphatidylethanolamine.

What is claimed is:

1. A compound having a formula:

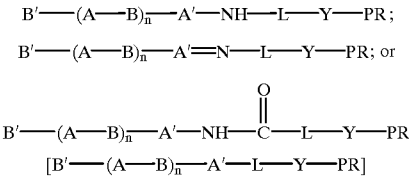

wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is an acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide;

Y is selected from the group consisting of a methylene radical, β-hydroxyethylene radical, carboxyl radical, succinimide α radical, and a covalent bond; and PR is a prosthetic surface.

2. The compound of claim 1 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

3. The compound of claim 1 wherein said sugars A and B are selected from the group consisting of N-acetylgalactosamine, N-acetylglucosamine, glucuronic acid, iduronic acid, and glucose.

4. The compound of claim 1 wherein said prosthetic surface is a synthetic polymer or a tissue-derived prosthetic surface.

5. A method for masking biologically reactive sites on the surface of a synthetic polymeric or tissue derived prothesis comprising reacting nucleophilic moieties on a surface of a polymeric or tissue-derived prosthesis with a masking molecule having a formula:

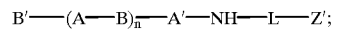
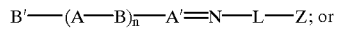
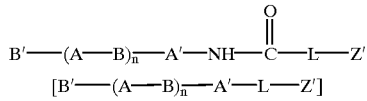
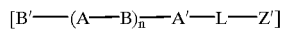

wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is an acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Z' to the 1-amino, 1-amido or 1-imino group attached to C-1 of sugar A', the aliphatic, acyclic carbon chain containing one or more moieties selected from the group consisting of ether, thio ether, and amide; and Z' is selected from the group consisting of an aldehyde, an activated ester of a carboxylic acid, a maleimide, an epoxide, a tosyl ester, a tresyl ester, and a halide.

6. The compound of claim 5 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

7. The compound of claim 5 wherein said sugars A and B are selected from the group consisting of N-acetylgalactosamine, N-acetylglucosamine, glucuronic acid, iduronic acid, and glucose.

8. A liposome composition comprising a mixture of a phospholipid and cholesterol in an aqueous phase, wherein the phospholipid has the formula:

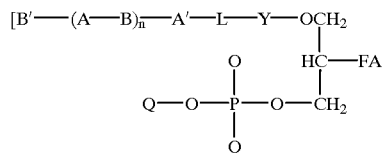

and

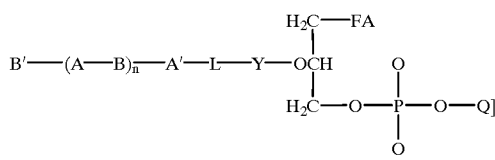

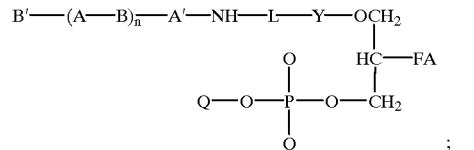

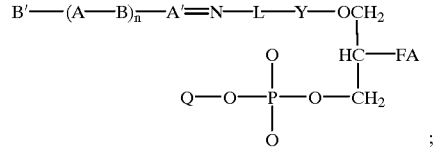

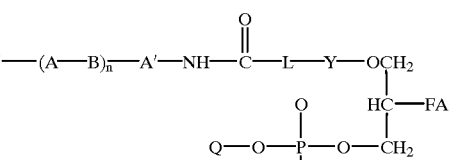

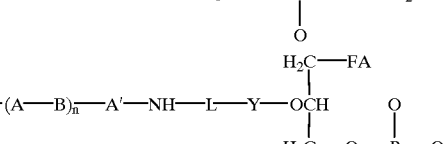

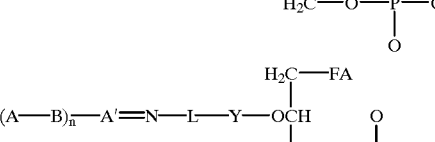

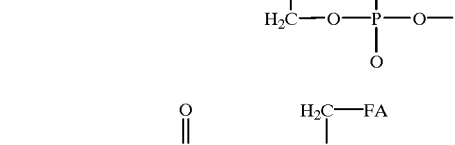

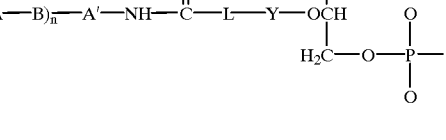

; or

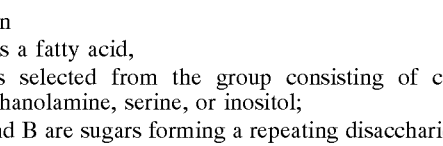

wherein

FA is a fatty acid,

Q is selected from the group consisting of choline, ethanolamine, serine, or inositol;

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is an acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide; and Y is an acyl radical.

9. The composition of claim 8 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

10. The composition of claim 8 wherein said sugars A and B are selected from the group consisting of N-acetylgalactosamine, N-acetylglucosamine, glucuronic acid, iduronic acid, and glucose.

11. A compound comprising a prosthetic polymer having a polyolefinic surface and an oligosaccharide adsorbed to said polyolefinic surface by electrostatic interaction, said oligosaccharide having a formula:

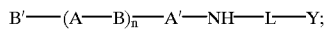
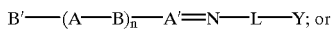
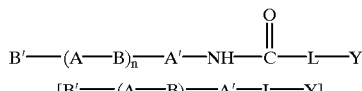
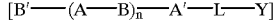

wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is an acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide; and Y is a linear n-alkyl radical having 5 to 30 carbon atoms.

12. The compound of claim 11 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

13. The compound of claim 11 wherein said sugars A and B are selected from the group consisting of N-acetylgalactosamine, N-acetylglucosamine, glucuronic acid, iduronic acid, and glucose.

14. A compound comprising a prosthetic polymer having a surface and an oligosaccharide adsorbed to said surface, said oligosaccharide having the formula:

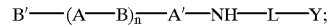
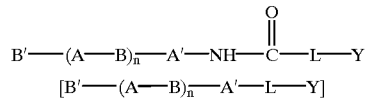
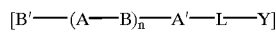

wherein

A and B are sugars forming a repeating disaccharide unit in which A and B are joined covalently by a glycosidic bond between C-1 of sugar A and C-3 or C-4 of sugar B, and the repeating disaccharide units are joined covalently to form an oligosaccharide by a glycosidic bond between C-1 of sugar B of a first disaccharide unit and C-3 or C-4 of sugar A in a next successive disaccharide unit, B' is a sugar at a non-reducing terminus of said oligosaccharide of ring structure identical to sugar B, A' is an acyclic hexose joined covalently by a glycosidic bond between C-1 of sugar B at a terminus opposite the non-reducing terminus of said oligosaccharide and C-3 or C-4 of sugar A', n is an integer from 2 to 20, L is an aliphatic, acyclic carbon chain which links Y to the 1-amino, 1-amido or 1-imino group attached to C-1 of sugar A', the aliphatic, acyclic carbon chain containing one or more moieties selected from the group consisting of ether, thio ether, and amide; and Y is a linear perfluoronated radical having 5 to 30 carbon atoms.

15. The compound of claim 14 wherein said oligosaccharide is an acid hydrolyzed polysaccharide selected from the group consisting of chondroitin-4-sulfate, chondroitin-6-sulfate, and hyaluronic acid in a molecular size range of 1,000 to 15,000 daltons.

16. The compound of claim 14 wherein said sugars A and B are selected from the group consisting of N-acetylgalactosamine, N-acetylglucosamine, glucuronic acid, iduronic acid, and glucose.

* * * * *

UNITED STATES PATENT AND TRADEMARK OFFICE
CERTIFICATE OF CORRECTION

PATENT NO. : 6,204,254 B1 Page 1 of 1
DATED : March 20, 2001
INVENTOR(S) : Deanna J. Nelson et al.

It is certified that error appears in the above-identified patent and that said Letters Patent is hereby corrected as shown below:

Column 12,

Line 40, "[B' - (A-B)$_n$ - A' - L - Y - PR]" should have been deleted.

Column 13,

Line 27, "[B' - (A-B)$_n$ - A' - L - Z']" should have been deleted.

Column 14,

Lines 2-14, "[B' - (A-B)$_n$ - A' - L - Y - OCH$_2$

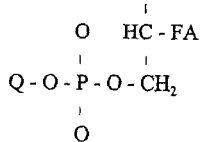

and

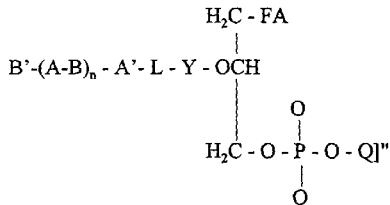

should have been deleted.

Signed and Sealed this

Seventeenth Day of June, 2003

JAMES E. ROGAN
*Director of the United States Patent and Trademark Office*